US006309654B1

(12) United States Patent
Hörner et al.

(10) Patent No.: US 6,309,654 B1
(45) Date of Patent: Oct. 30, 2001

(54) ACTIVATED OXYGEN CONTAINING COMPOUNDS FOR IMPROVING THE MICROCIRCULATION OF THE SKIN

(75) Inventors: Wolf-Dieter Hörner, Berlin; Klaus Gäbelein, Grafrsth, both of (DE)

(73) Assignee: Gabriele Wyeth Ohg Kosmetik Berlin (DE)

( * ) Notice: Subject to any disclaimer, the term of this patent is extended or adjusted under 35 U.S.C. 154(b) by 0 days.

(21) Appl. No.: 09/296,870

(22) Filed: Apr. 22, 1999

(30) Foreign Application Priority Data

Apr. 23, 1998 (DE) ................................................ 198 18 914

(51) Int. Cl.[7] ...................................................... A61K 6/00
(52) U.S. Cl. ............................ 424/401; 424/45; 514/714; 514/937; 514/938; 514/944
(58) Field of Search ..................... 424/401, 45; 514/714, 514/937, 938, 944

(56) References Cited

U.S. PATENT DOCUMENTS 4,591,602 * 5/1986 De Villez .............................. 424/278

FOREIGN PATENT DOCUMENTS

| 1668144 | * | 11/1976 | (DE) . |
| 3643323 | * | 6/1988 | (DE) . |
| 36 43 323 C2 | | 6/1988 | (DE) . |

OTHER PUBLICATIONS

Del Maestro et al. Free radicals as mediators of tissue injury. Acta Phisol. Scand. Supplementum, 492, 43–57, 1980.*

* cited by examiner

*Primary Examiner*—Thurman K. Page
*Assistant Examiner*—Lakshmi Channavajjala
(74) *Attorney, Agent, or Firm*—McGlew and Tuttle, P.C.

(57) ABSTRACT

The present invention pertains to the use of a cosmetically and dermatologically well-tolerated organic compound containing activated oxygen for preparing a preparation for improving the microcirculation of the skin.

6 Claims, No Drawings

ACTIVATED OXYGEN CONTAINING COMPOUNDS FOR IMPROVING THE MICROCIRCULATION OF THE SKIN

FIELD OF THE INVENTION

The present invention pertains to an agent for improving the microcirculation of the skin, which contains as the active ingredient at least one cosmetically and pharmaceutically well-tolerated organic compound containing activated oxygen.

BACKGROUND OF THE INVENTION

Compounds containing activated oxygen are defined as compounds into which a peroxide group has been introduced, preferably by means of ozone.

It has been known, e.g., that so-called ozonides are formed during the ozonization of olefinically unsaturated organic compounds, but these ozonides have, in general, low stability. However, if the ozonization is carried out in the presence of a solvent containing hydroxyl groups, stable compounds, the acetal peroxides, are obtained (DE-B 10 75 801, DE-B 11 66 975, DE-A 16 68 144, and DE-A 41 13 389).

It has also been known that peroxyaldehydes and peroxycarboxylic acids can be prepared by the oxidation of saturated alcohols, aldehydes or ketones with ozone gas or ozone-containing gases (DE-A 36 43 323).

These compounds have been described as having a potent bactericidal action, which is accompanied by an excellent skin tolerance. It has therefore been suggested that they be used as disinfectants in cosmetics and pharmaceutical products, for wound healing, e.g., for the treatment of antibiotic-resistant purulent fistulae, and as an oxygen supplier for the skin (DE-B 10 75 801, DE-A 16 68 144, K. G äbelein, *Seifen, Öle, Wachse,* Vol. 112, p. 17, 1986).

However, the effect of these compounds on the microcirculation of the skin is not mentioned in any of the said documents.

Microcirculation is defined as the subcutaneous blood circulation extending subcutaneously in the area of the capillary system, the section of the vascular system comprising arterioles, capillaries and postcapillary veins (venules).

The nutritive blood supply by oxygen exchange between blood and tissue as well as the maintenance of the thermal and ionic environment take place via this subcutaneous blood circulation. Disturbances in the microcirculation therefore greatly affect the supply of essential substances for the tissues.

For example, the suspension stability of the blood decreases in the case of decelerated flow, which leads to plasma "skimming," a phenomenon in which partial or complete separation of plasma and cellular elements of the blood takes place at the branchings of the capillaries, so that only plasma flows through individual capillaries, as a result of which the supply is compromised in these areas.

Thus, the microcirculation of the skin substantially affects the function of the skin and is closely linked with the aging of the skin.

SUMMARY AND OBJECTS OF THE INVENTION

The object of the present invention is to provide an agent that can improve the microcirculation of the skin and is consequently able to favorably stimulate the skin functions.

It has now been found in a completely surprising manner that organic compounds containing activated oxygen are able to increase the microcirculation of the skin and thus support the undisturbed flow of blood and the supply of the skin with important nutrients. Especially favorable effects were able to be demonstrated for the stressed and aging skin.

Thus, the present invention pertains to an agent for improving the microcirculation of the skin, which contains as the active ingredient at least one cosmetically and dermatologically well-tolerated organic compound containing activated oxygen.

Such compounds will hereinafter also be called compounds with activated oxygen.

This agent is particularly suitable for promoting the supply of the stressed and aging skin. Supporting of the undisturbed blood flow, as a result of which possible disturbances can be prevented, is to be emphasized in relation to youthful or young skin.

The agent can be used successfully in a broad range of applications, e.g., in cosmetics, pharmaceutics, especially dermatology, as well as the cosmetic and medical treatment of animals.

The organic compounds containing activated oxygen according to the present invention are compounds containing a peroxide group, which are cosmetically and dermatologically well tolerated.

The examples of such compounds include acetal peroxides. Particularly suitable representatives as well as processes for preparing same are described in DE-B 10 75 801, DE-B 11 66 975, DE-A 16 68 144, and DE-A 41 13 389, which are hereby incorporated by reference.

The acetal peroxides preferred according to the present invention are obtained by the ozonization of olefinically unsaturated organic compounds in the presence of alcohols or polyols, such as glycols, polyglycols and glycerol. In this case, the alcohol and the polyol participate in the reaction, and hemiacetals are formed

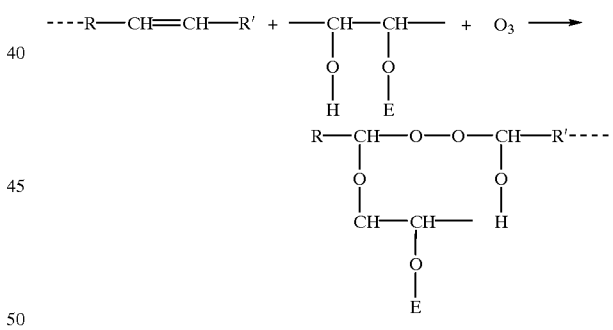

in which R and R', which are identical or different, denote, independently from one another, an organic radical, which may be a C1–C30 hydrocarbon, C1–C30 alcohol, C1–C30 aldehyde, C1–C30 ketone, C1–C30 acid or its ester, and E denotes a radical of an organic alcohol or an acid, or a C1–C10 and preferably a C1–C4 alkyl or R"—CO—, in which R" preferably denotes a C1–C10 alkyl, e.g., a C1–C4 alkyl.

Preferred examples of the unsaturated organic compound are unsaturated fatty acids and their esters, such as sorbic acid, oleic acid, oleyl oleate, linoleic acid ethyl ester, castor oil, olive oil, soybean oil, etc., as well as terpineol, wherein sorbic acid is particularly preferred.

The suitable alcohols include, e.g., lower alcohols, especially C1–C6 monohydric alcohols, methanol, ethanol, and propyl alcohol.

Partially esterified or etherified polyols, such as glycols and polyglycols, e.g., ethylene, propylene and butylene glycols, as well as glycerol may be used especially advantageously for the reaction with the olefinically unsaturated compound. The examples of these are ethyl, propyl and butyl glycol ethers, ethyl diglycol, 1,2-propylene glycol monoethyl ether, and glycerol diacetate.

An acetal peroxide that is obtained from sorbic acid in ethyl diglycol is particularly preferred according to the present invention.

Furthermore, peroxyaldehydes and peroxycarboxylic acids, as they are described, e.g., in DE-A 36 43 323, which is referred to in full, may be used as well.

Combinations of different compounds with activated oxygen may also be used.

Contrary to the industrial peroxides, which are corrosive and toxic for the skin, such as hydrogen peroxide, the compounds used according to the present invention are definitely well tolerated by the skin and nontoxic.

This extraordinarily good skin tolerance can be attributed to the fact that the compounds containing activated oxygen according to the present invention are compounds similar to those formed in nature as well when atmospheric ozone is bound to plant materials in the presence of compounds containing hydroxyl groups.

The agents according to the present invention for improving the microcirculation of the skin may, of course, also contain, besides the compound containing activated oxygen, additional carriers, active ingredients and additives which are usually used in such agents and are determined by the desired application of the agent or of the compound containing activated oxygen.

These additives as well as the formulation processes are selected according to the usual methods well known to the galenic expert.

The agent may be used in any desired application form, e.g., in an aqueous or alcohol solution, mixed forms thereof, in the solid or nonsolid form, as an oil-in-water emulsion or a water-in-oil emulsion and mixed forms thereof, as microemulsions, gels, etc. It may be used, e.g., as a cream, oil, spray, foam aerosol, or as a bath additive.

The percentage of the compound containing activated oxygen in the agent varies depending on the intended use as well as the application form.

It has proved to be sufficient, in general, to add the compound to the agent in an amount of 0.5 wt. % to 20 wt. % relative to the total weight of the agent.

The percentage is preferably 1 wt. % to 12 wt. % and especially preferably 2 wt. % to 8 wt. % and especially 3 wt. % to 6 wt. %.

If the agent is diluted during the application, e.g., in the case of a bath additive, the percentage of the compound containing activated oxygen may be up to 20 wt. %. The percentage may, of course, also be higher if necessary.

In another embodiment, the agent additionally contains saturated and/or unsaturated fatty acids and/or their esters, besides the compound containing active oxygen.

Examples of this are the fatty acids and fatty acid esters, which are described above in connection with the preparation of the compound containing activated oxygen.

The percentage of fatty acid and/or fatty acid ester may be on the same order of magnitude as described above for the compound containing activated oxygen.

The favorable effect on the skin and, moreover, the stability of the fatty acid/ester can be increased by the combined use of the compound containing activated oxygen and the fatty acid/ester.

The acetal peroxides used according to the present invention may advantageously also be used in a solution in an alcohol, polyol, partially esterified or partially etherified polyols, as they were described above for the preparation of the acetal peroxides as such or with additional additives.

For example, the acetal peroxide of sorbic acid, which is preferred according to the present invention, is used with ethylene diglycol in the form of its 4% solution in ethyl diglycol (Ozonid SV®) in an embodiment that is especially preferred according to the present invention.

DESCRIPTION OF EXAMPLES OF THE INVENTION

The present invention will be illustrated below on the basis of the example of the effect of the agent according to the present invention on the microcirculation of the skin.

The test subjects were women in the age bracket of 46 to 55 years with normal and healthy skin (so-called average type). Two different pairs of test and control areas each were selected on the right and left shoulder areas, the test substance was applied to the test areas, and the change in the microcirculation was determined in comparison with the control areas, to which no test substance had been applied.

The application of the test substances was performed by taking into account DIN 67 501 (December 1985): Experimental Dermatological Evaluation of the Protection from Erythema by External Sunscreens for the Human Skin."

The evaluation was always performed before and after the application of the test substance, using an intravital microscopic investigation unit according to the combined incident light and transmitted light method with selective light generators and selective filtration.

A care cream containing Ozonid SV® was used as the test substance.

As a result, an increase in the mean flow rate of red blood cells in the capillary flows and an improvement in the distribution of blood in the microcirculation of the skin were seen upon the application of the care cream Ozonid SV®, as a result of which the functional status of the microcirculation in the skin was favorably affected.

The present invention provides for the use of a cosmetically and dermatologically well-tolerated organic compound containing activated oxygen for preparing a preparation for improving the microcirculation of the skin and for using an effective amount of this material to improve the microcirculation if the skin. The compound preferably contains activated oxygen obtained by ozonizing an organic compound. The compound containing activated oxygen may be selected from the group comprising acetal peroxide, peroxyaldehyde, peroxycarboxylic acid and mixtures of these compounds. The acetal peroxide can be prepared by ozonizing a saturated or unsaturated fatty acid or an ester thereof in the presence of a partially etherified or partially esterified Polyol. The acetal peroxide can be prepared by ozonizing sorbic acid in ethyl diglycol. The pharmaceutical composition which is used contains a compound according to one or more of the features mentioned above and a fatty acid and/or an ester thereof. The above explanations regarding the agent correspondingly concern the use according to the present invention and the pharmaceutical composition according to the present invention. The same also applies to the method for preparing the material for improving the microcirculation of the skin, wherein cosmetically and dermatologically well-tolerated organic compound containing activated oxygen is mixed with usual galenic carriers or ointment carriers, and preferably wherein the compound contains activated oxygen prepared by ozonizing an organic compound and/or where the compound contains activated oxygen and is selected from the group comprising acetal peroxide, peroxyaldehyde, peroxycarboxylic, mixtures of these compounds and optionally with the acetal peroxide being prepared by ozonizing a saturated or a unsaturated fatty acid or an esther thereof in the presence of a partially etherified or partially esterified Polyol and are optionally the acidal peroxide can prepared by ozonizing sorbic acid in ethyl diglycol, according to which a process for preparing an agent or preparation according to the present invention as well as a process for improving the microcirculation of the skin are taught. Concerning the process for improving the microcirculation, the explanations regarding the agent or the preparation apply correspondingly. Concerning the carriers in question, reference is made to the above statements on the presentations. All types of ointment bases or bases or foundations are called ointment carriers, regardless of whether ointments, creams or pastes are to be prepared with them. Ointment carriers function as carriers or vehicles for active ingredients and they promote their penetration or resorption. Ointment carriers are well known to the person skilled in the art, in connection with which reference is expressly made, e.g., only to the reference Römpp, *Chemie Lexikon* [Encyclopedia of Chemistry], paperback edition, Vol. 5, 1995, page 3969.

What is claimed is:

1. A method for improving the microcirculation of the skin of a subject having normal and healthy skin and whose skin microcirculation is sought to be improved, which comprises externally applying to said skin of said subject a pharmaceutical composition comprising a cosmetically and dermatologically well-tolerated organic compound comprising activated oxygen which is selected from the group consisting of acetal peroxide, peroxyaldehyde, peroxycarboxylic acid, and mixtures of these compounds, in an effective amount for improving the microcirculation of said skin of said subject.

2. A method according to claim 1 wherein said organic compound comprising activated oxygen is acetal peroxide, and the acetal peroxide is obtained by ozonizing a saturated or unsaturated fatty acid or an ester thereof in the presence of a partially etherified or partially esterified polyol.

3. A method according to claim 2 wherein the acetal peroxide is obtained by ozonizing sorbic acid in ethyl diglycol.

4. A method according to claim 1 wherein the pharmaceutical composition comprises (a) said organic compound comprising activated oxygen, in combination with (b) at least one further compound selected from the group consisting of a fatty acid, an ester thereof, and mixtures of these compounds.

5. A method according to claim 2 wherein the pharmaceutical composition comprises (a) said organic compound comprising activated oxygen, in combination with (b) at least one further compound selected from the group consisting of a fatty acid, an ester thereof, and mixtures of these compounds.

6. A method according to claim 3 wherein the pharmaceutical composition comprises (a) said organic compound comprising activated oxygen, in combination with (b) at least one further compound selected from the group consisting of a fatty acid, an ester thereof, and mixtures of these compounds.

* * * * *